(12) United States Patent
Miller et al.

(10) Patent No.: US 9,592,358 B2
(45) Date of Patent: Mar. 14, 2017

(54) RESPIRATORY INTERFACE DEVICES

(75) Inventors: Andrew Miller, Bracknell (GB);
Martin Spayne, Guernsey (GB);
Martin Davies, Farnborough (GB)

(73) Assignee: Intersurgical AG, Vaduz (LI)

( * ) Notice: Subject to any disclaimer, the term of this patent is extended or adjusted under 35 U.S.C. 154(b) by 413 days.

(21) Appl. No.: 12/996,349

(22) PCT Filed: Jun. 1, 2009

(86) PCT No.: PCT/GB2009/050599
§ 371 (c)(1),
(2), (4) Date: Mar. 28, 2011

(87) PCT Pub. No.: WO2009/147424
PCT Pub. Date: Dec. 10, 2009

(65) Prior Publication Data
US 2011/0162650 A1   Jul. 7, 2011

Related U.S. Application Data (60) Provisional application No. 61/059,067, filed on Jun. 5, 2008.

(30) Foreign Application Priority Data

Jun. 4, 2008   (GB) .................................... 0810169.3

(51) Int. Cl.
*A62B 18/02*   (2006.01)
*A61M 16/00*   (2006.01)
*A61M 16/04*   (2006.01)

(52) U.S. Cl.
CPC ........ *A61M 16/04* (2013.01); *A61M 16/0409* (2014.02); *A61M 16/0434* (2013.01); *A61M 16/0497* (2013.01)

(58) Field of Classification Search
CPC .......... A61M 16/04; A61M 2016/0409; A61M 16/0434; A61M 16/044; A61M 16/06;
(Continued)

(56) References Cited

U.S. PATENT DOCUMENTS

| 2,099,127 A | 11/1937 | Leech |
| 3,659,612 A * | 5/1972 | Shiley ............... A61M 16/0465 128/207.15 |

(Continued)

FOREIGN PATENT DOCUMENTS

| CA | 1324551 | 11/1993 |
| CA | 2346248 A1 | 4/2000 |

(Continued)

OTHER PUBLICATIONS

UKIPO Search Report for Great Britain Appl. No. 0909304.8, filed Jun. 1, 2009.

(Continued)

*Primary Examiner* — Tan-Uyen (Jackie) T Ho
*Assistant Examiner* — Ned T Heffner
(74) *Attorney, Agent, or Firm* — LeClairRyan, a Professional Corporation (57) ABSTRACT

A respiratory interface device (10, 20, 30, 40, 50, 60, 70, 80) comprising a main body (12, 22, 32, 42, 52, 62, 72, 82) that includes a fluid conduit adapted to be connected to a breathing circuit, and a sealing member (15, 25, 35, 45, 55, 65, 75, 85) adapted to engage a surface of a patient, such that the fluid conduit is in fluid communication, in use, with an airway of the patient, wherein the sealing member (15, 25, 35, 45, 55, 65, 75, 85) includes a plasticizing agent, and a barrier member (18, 28, 38, 48, 58, 68, 78, 88) is provided between the sealing member (15, 25, 35, 45, 55, 65, 75, 85) and the main body (12, 22, 32, 42, 52, 62, 72, 82) of the device (10, 20, 30, 40, 50, 60, 70, 80), the barrier member (Continued)

(18, 28, 38, 48, 58, 68, 78, 88) at least impeding the migration of plasticizing agent from the sealing member (15, 25, 35, 45, 55, 65, 75, 85) to the main body (12, 22, 32, 42, 52, 62, 72, 82) of the device (10, 20, 30, 40, 50, 60, 70, 80).

8 Claims, 5 Drawing Sheets

(58) Field of Classification Search
CPC ...... A61M 16/0683; A61M 2016/0616; A61M 16/08
USPC .......................... 128/200.24, 200.26, 207.11, 128/207.13–207.18, 205.25, 206.21, 128/206.24, 206.25
See application file for complete search history.

(56) References Cited

U.S. PATENT DOCUMENTS

| | | | |
|---|---|---|---|
| 3,734,100 A | | 5/1973 | Walker et al. |
| 4,289,128 A | * | 9/1981 | Rusch ...................... 128/207.15 |
| 4,509,514 A | | 4/1985 | Brain |
| 4,790,306 A | | 12/1988 | Braun et al. |
| 4,995,388 A | | 2/1991 | Brain |
| 5,241,956 A | | 9/1993 | Brain |
| 5,249,571 A | | 10/1993 | Brain |
| 5,282,464 A | | 2/1994 | Brain |
| 5,297,547 A | | 3/1994 | Brain |
| 5,303,697 A | | 4/1994 | Brain |
| 5,305,743 A | | 4/1994 | Brain |
| 5,355,879 A | | 10/1994 | Brain |
| 5,391,248 A | | 2/1995 | Brain |
| 5,477,851 A | | 12/1995 | Callaghan et al. |
| 5,584,290 A | | 12/1996 | Brain |
| 5,623,921 A | | 4/1997 | Kinsinger et al. |
| 5,632,271 A | | 5/1997 | Brain |
| 5,647,357 A | * | 7/1997 | Barnett et al. ........... 128/206.24 |
| 5,655,519 A | | 8/1997 | Alfery |
| 5,682,880 A | | 11/1997 | Brain |
| 5,762,638 A | * | 6/1998 | Shikani ................ A61K 9/0024 128/207.14 |
| 5,771,293 A | | 6/1998 | Schneider |
| 5,791,341 A | | 8/1998 | Bullard |
| 5,878,745 A | | 3/1999 | Brain |
| 5,881,726 A | | 3/1999 | Neame |
| 5,896,858 A | | 4/1999 | Brain |
| 5,921,988 A | | 7/1999 | Legrand |
| 5,937,859 A | | 8/1999 | Augustine et al. |
| 5,937,860 A | | 8/1999 | Cook |
| 5,964,217 A | | 10/1999 | Christopher |
| 5,988,167 A | | 11/1999 | Kamen |
| 6,003,514 A | | 12/1999 | Pagan |
| 6,055,984 A | | 5/2000 | Brain |
| 6,070,581 A | | 6/2000 | Augustine et al. |
| 6,079,409 A | | 6/2000 | Brain |
| D429,811 S | | 8/2000 | Bermudez |
| 6,095,144 A | | 8/2000 | Pagan |
| 6,152,136 A | | 11/2000 | Pagan |
| 6,280,675 B1 | | 8/2001 | Legrand |
| 6,318,367 B1 | | 11/2001 | Mongeon |
| 6,397,847 B1 | | 6/2002 | Scarberry et al. |
| 6,431,219 B1 | * | 8/2002 | Redler .................. A61L 29/085 138/137 |
| 6,439,232 B1 | | 8/2002 | Brain |
| 6,474,332 B2 | | 11/2002 | Arndt |
| 6,604,525 B2 | | 8/2003 | Pagan |
| 6,631,720 B1 | | 10/2003 | Brain |
| 6,679,263 B2 | | 1/2004 | Luchetti et al. |
| 6,698,430 B2 | | 3/2004 | Van Landuyt |
| 6,705,318 B1 | | 3/2004 | Brain |
| 6,792,948 B2 | | 9/2004 | Brain |
| 6,918,388 B2 | | 7/2005 | Brain |
| 7,040,312 B2 | | 5/2006 | Alfery et al. |
| 7,263,998 B2 | | 9/2007 | Miller |
| 2001/0015207 A1 | | 8/2001 | Pagan |
| 2002/0010417 A1 | | 1/2002 | Bertram |
| 2002/0012728 A1 | | 1/2002 | Carlson et al. |
| 2002/0078961 A1 | | 6/2002 | Collins |
| 2002/0100479 A1 | | 8/2002 | Scarberry et al. |
| 2002/0170556 A1 | | 11/2002 | Gaitini |
| 2003/0037790 A1 | | 2/2003 | Brain |
| 2003/0066532 A1 | | 4/2003 | Gobel |
| 2003/0101998 A1 | | 6/2003 | Zocca et al. |
| 2003/0136413 A1 | | 7/2003 | Brain et al. |
| 2003/0172925 A1 | | 9/2003 | Zocca et al. |
| 2003/0172933 A1 | | 9/2003 | Nimmo |
| 2003/0172935 A1 | * | 9/2003 | Miller .................. A61M 16/04 128/207.15 |
| 2004/0020488 A1 | | 2/2004 | Kniewasser |
| 2004/0020491 A1 | | 2/2004 | Fortuna |
| 2005/0051173 A1 | | 3/2005 | Brain |
| 2005/0051175 A1 | | 3/2005 | Brain |
| 2005/0066975 A1 | | 3/2005 | Brain |
| 2005/0103345 A1 | | 5/2005 | Brain |
| 2006/0081245 A1 | | 4/2006 | Gould |
| 2008/0078404 A1 | | 4/2008 | Martens |

FOREIGN PATENT DOCUMENTS

| | | |
|---|---|---|
| CA | 2191749 | 2/2002 |
| CN | 1166138 A | 11/1997 |
| CN | 1351509 | 5/2002 |
| DE | 19500550 A1 | 7/1996 |
| DE | 29902267 U1 | 9/1999 |
| DE | 20100176 U1 | 6/2001 |
| DE | 20206692 U1 | 9/2002 |
| DE | 102005009577 A1 | 8/2006 |
| EP | 0277797 A2 | 8/1988 |
| EP | 0389272 A2 | 9/1990 |
| EP | 0448878 A2 | 10/1991 |
| EP | 0794807 B1 | 9/1997 |
| EP | 0857492 A2 | 1/1998 |
| EP | 0834331 A2 | 4/1998 |
| EP | 0911049 A1 | 4/1999 |
| EP | 0935971 A2 | 8/1999 |
| EP | 1125595 A1 | 8/2001 |
| ES | 1046206 U | 12/2000 |
| GB | 2168256 A | 6/1986 |
| GB | 2249959 A | 5/1992 |
| GB | 2267034 A | 11/1993 |
| GB | 2285765 A | 7/1995 |
| GB | 2317342 A | 3/1998 |
| GB | 2337020 A | 11/1999 |
| GB | 2359996 A | 9/2001 |
| GB | 2364644 A | 2/2002 |
| GB | 2373188 A | 9/2002 |
| GB | 2393399 A | 3/2004 |
| GB | 2404863 A | 2/2005 |
| IE | 922073 | 12/1993 |
| WO | 94/17848 A1 | 8/1994 |
| WO | 98/50096 A1 | 11/1998 |
| WO | 99/24101 A1 | 5/1999 |
| WO | 00/30706 A1 | 6/2000 |
| WO | 00/61213 A1 | 10/2000 |
| WO | 01/97890 A1 | 12/2001 |
| WO | 02/13884 A | 2/2002 |
| WO | 02/32490 A2 | 4/2002 |
| WO | 03/016018 A1 | 2/2003 |
| WO | 2004/016308 A2 | 2/2004 |

OTHER PUBLICATIONS

ISA210 EPO Search Report for PCT/GB2009/050599, filed Jun. 1, 2009.

* cited by examiner

RESPIRATORY INTERFACE DEVICES

This application is a national stage application under 35 U.S.C. §371 of PCT/GB2009/050599, filed Jun. 1, 2009, which claims priority of U.S. Provisional Patent Application Ser. No. 61/059,067, filed Jun. 5, 2008, and GB Patent Application No. 0810169.3, filed Jun. 4, 2008.

The present invention relates to respiratory interface devices and associated methods of manufacture.

Respiratory apparatus generally includes some form of respiratory interface device in order to connect the respiratory apparatus to the respiratory system of a patient. There are a wide range of different interface devices, including non-invasive interface devices, such as face masks and nasal masks, and also invasive interface devices, such as endotracheal tubes, tracheostomy tubes and laryngeal mask airways.

Many of these interface devices are adapted to seal against a surface of the patient's body, which may be an external or internal surface, in order to form an effective seal with an airway of the patient. For example, non-invasive interface devices typically include a sealing member that seals the device to the face of the patient, thereby forming an effective connection between the device and the mouth and/or nose of the patient, and invasive interface devices often include a sealing member that seals the device to an interior surface of an airway of the patient, thereby forming an effective connection between the device and that airway.

Although it has been known for some time to use an inflatable member as a sealing member, a relatively recent development in relation to respiratory interface devices is the use of a very compliant, soft, non-inflatable member as a sealing member. In order to achieve a desired compliancy and softness of the non-inflatable sealing member, it is typically necessary to include additives in the material of the sealing member, such as plasticising agents. However, it has been found that these non-inflatable sealing members can become distorted over time, for example following a prolonged period of storage.

There has now been devised an improved respiratory interface device and associated method of manufacture which overcome or substantially mitigate the above-mentioned and/or other disadvantages associated with the prior art.

According to a first aspect of the invention, there is provided a respiratory interface device comprising a main body that includes a fluid conduit adapted to be connected to a breathing circuit, and a sealing member adapted to engage a surface of a patient, such that the fluid conduit is in fluid communication, in use, with an airway of the patient, wherein the sealing member includes a plasticising agent, and a barrier member is provided between the sealing member and the main body of the device, the barrier member at least impeding the migration of plasticising agent from the sealing member to the main body of the device.

The respiratory interface device according to the present invention is advantageous principally because the barrier impedes, and most preferably substantially prevents, the migration of plasticiser from the sealing member to the main body of the device. This feature reduces the risk of the condition of the sealing member deteriorating over time, and hence becoming less effective at sealing the device to the patient. In particular, this feature reduces the risk of the sealing member changing shape over time, for example becoming distorted or shrunken, and reduces the risk of the sealing member becoming harder and/or less compliant over time.

The present invention is advantageous in relation to any respiratory interface device in which the arrangement of the device is such that plasticising agent would migrate from the sealing member to the main body of the device, if the barrier member were absent. In particular, the main body of the device may not include any plasticising agent. Alternatively, the main body of the device may include a plasticising agent, but in a lower concentration in comparison to the sealing member.

The sealing member is preferably non-inflatable. In particular, the sealing member is preferably formed of a unitary body of material, which is preferably sufficiently deformable to effectively seal against a surface of the patient. The sealing member is preferably also soft in compression to avoid undue damage to the patient. In particular, the sealing member will typically have a Shore hardness on the A scale of less than 40. Suitable materials for the sealing member include silicone rubbers and thermoplastic elastomers, such as the styrene block copolymers (eg Styrene Butadiene Styrene (SBS), and Styrene Ethylene Butylene Styrene (SEBS)), Thermoplastic Olefin Blends (TPO), Thermoplastic PolyUrethanes (TPU), Copolyester (COPE), Polyether Block Amides (PEBAX) and foamed versions thereof, and Polyvinylchloride (PVC).

The sealing member is preferably more deformable than the main body of the device. In order to achieve the desired deformability, the sealing member includes a plasticising agent, which may be a single substance, or a mixture of two or more different substances. The plasticising agent will typically be an oil-based plasticising agent, such as white paraffin oil.

The barrier may be formed of any suitable material, such as plastics or metal, but is most preferably formed of a plastics material. The composition of the barrier is preferably selected as the most appropriate for the materials of the sealing member and the main body of the device, and also the effectiveness of barrier needed for the particular plasticising agent. The barrier is preferably formed of a different material to both the material of the sealing member and the material of the main body of the device. However, the barrier is preferably adapted to bond to both the sealing member and the main body of the device. The barrier may comprise a single material, such as polypropylene or low-density polyethylene, that is adapted to bond to both the sealing member and the fluid conduit, as well as substantially prevent the migration of plasticising agent therethrough. Alternatively, the barrier may comprise two or more different materials, which may be arranged in a plurality of layers. For instance, in presently preferred embodiments, the barrier comprises an intermediate portion or layer of a material, such as Ethylene Vinyl Alcohol (EVOH), that is adapted to substantially prevent the migration of plasticising agent therethrough, and outer portions or layers on both sides of the intermediate portion or layer that are adapted to bond to both the sealing member and the fluid conduit.

The barrier member may have any suitable form, such as a substantially planar film, a shaped film, a tubular barrier, or a more substantial body of material. The barrier may be adapted such that there is no direct contact between the sealing member and the main body of the device. In this configuration, the barrier preferably comprises a first engagement surface to which the sealing member is bonded, and a second engagement surface to which the main body of the device is bonded.

Alternatively, where the selection of materials causes the bond strength between the barrier and the sealing member, and/or the bond strength between the barrier and the main body of the device, to be insufficient for this configuration, the barrier may be adapted such that there is at least some contact, and most preferably at least some bonding, between the sealing member and the main body of the device. For instance, the barrier member may include one or more apertures through which one or more projections of the sealing member and/or the main body of the device project into the other component. In this configuration, the projections of the sealing member and/or the main body of the device are preferably bonded to the other component.

The barrier member preferably extends across the entire extent of the interface between the sealing member and the main body of the device. The barrier member may extend beyond this interface, but most preferably the external surfaces of the barrier member are co-extensive with the external surfaces of the sealing member and/or the main body of the device.

The main body of the device may be formed of a similar material to the material of the sealing member. In particular, the main body of the device may also include a plasticising agent, but in a lower concentration in comparison to the sealing member.

The sealing member is preferably adapted to restrict, and preferably substantially prevent, the passage of respiratory gases from the interior of the fluid conduit into the atmosphere. In particular, the sealing member is preferably adapted to ensure that substantially no respiratory gas leaks into the atmosphere during positive pressure ventilation. The sealing member preferably therefore includes a continuous sealing surface that engages a continuous surface of the patient, in use.

The respiratory interface device according to the invention may be an invasive device and hence extend into an airway of the patient, during use, or a non-invasive device and hence not extend into an airway of the patient, during use. In either case, the respiratory interface device preferably includes a connector for connecting the fluid conduit to a breathing circuit. In addition, in the case of invasive respiratory interface devices, the sealing member preferably adapted to prevent the passage of pharyngeal contents into the trachea, and also to centre the fluid conduit within the associated airway of the patient. In the case of non-invasive respiratory interface devices, the sealing member is preferably also adapted to improve the comfort of the patient, during use, where pressure is applied to the face of the patient by the respiratory interface device.

Where the respiratory interface device is an invasive device, such as an endotracheal tube, a tracheostomy tube, or a laryngeal mask airway, the sealing member is preferably adapted to extend between an exterior surface of the gases airway and an interior surface of an airway of the patient. Most preferably, the sealing member extends about an exterior circumferential surface of the fluid conduit, and hence preferably occupies the space between the exterior circumferential surface of the fluid conduit and an adjacent circumferential surface of the internal surface of the patient's airway. The sealing member preferably has an exterior shape, in use, that matches that of the internal surface of the airway of the patient with which the sealing member with engage. Hence, before use, the sealing member preferably has an exterior shape that is readily deformable into a shape matches that of the internal surface of the airway of the patient with which the sealing member with engage. For example, where the respiratory interface device is an endotracheal tube or a tracheostomy tube, the exterior surface of the sealing member preferably has a substantially circular or elliptical cross-sectional shape, before use. Such a sealing member is commonly referred to as a "cuff".

In order to provide an effective seal with the airway of the patient, the sealing member of the invasive respiratory interface device is preferably readily deformable, so as to enable a range of different external dimensions to be adopted by the sealing member. Most preferably, the sealing member is adapted to be deformed by the interior surface of the airway into which it is inserted, in use, in order to provide a seal between the exterior surface of the fluid conduit and the interior surface of the airway of the patient.

Where the respiratory interface device is a non-invasive device, such as a face mask or a nasal mask, the sealing member is preferably adapted to extend from a portion of the device that surrounds an opening into the device. In particular, the opening, from about which the sealing member extends, preferably leads into a cavity of the device, preferably defined by a mask body, which is adapted to accommodate the mouth and/or nose of the patient. In addition, the mask body is preferably provided with a connector that enables the cavity of the mask body to be connected to a breathing circuit.

The sealing member of the non-invasive interface device is preferably continuous, and in particular preferably has a closed loop configuration. The sealing member is preferably adapted to seal against a continuous surface of the patient's face that surrounds the airway, for example the mouth and/or nose of the patient, with which the fluid conduit is adapted to be in fluid communication, in use.

In order to provide an effective seal with the face of the patient, the sealing member of the non-invasive respiratory interface device is preferably sufficiently deformable to enable the sealing member to match the contours of the patient's face. Most preferably, the sealing member is adapted to be deformed when pressed against the face of the patient, in use, in order to provide a seal between the cavity of the mask body and the mouth and/or nose of the patient.

According to a further aspect of the invention, there is provided a method of manufacturing a respiratory interface device, which method comprises the step of providing a barrier member between a main body and a sealing member of the device, the main body including a fluid conduit adapted to be connected to a breathing circuit, and the sealing member being adapted to engage a surface of a patient, such that the fluid conduit is in fluid communication, in use, with an airway of the patient, wherein the sealing member includes a plasticising agent, and the barrier member at least impedes the migration of plasticising agent from the sealing member to the main body of the device.

The method according to the invention preferably includes the step of bonding the barrier member to both the sealing member and the main body of the device. This step may be achieved by a variety of different methods, but most preferably the barrier member is bonded to the sealing member and the main body of the device whilst those components are incompletely cured or solidified.

In particular, the sealing member and/or the main body of the device are preferably formed by injection moulding those components directly onto associated engagement surfaces of the barrier member. In these embodiments, the sealing member and/or the main body of the device are preferably formed of a plastics material or a thermoplastic elastomer. The main body of the device is preferably injection moulded onto a first engagement surface of the barrier member, and the sealing member is preferably injection moulded onto a second engagement surface of the barrier member, these two injection moulding steps being performed in any order. The first and second engagement surfaces of the barrier member are preferably separate from each other, such that the sealing member and/or the main body of the device are not in direct contact with each other.

The barrier member may be located within a first mould cavity, before either the sealing member or the main body of the device is formed by injection moulding in that cavity. The sealing member or the main body of the device is preferably then formed by injection moulding in that cavity, such that that component bonds to the barrier member. The partially-formed device is preferably then transferred to a second mould cavity, and the remaining component, ie either the sealing member or the main body of the device, is preferably formed by injection moulding in that cavity, such that that component also bonds to the barrier member.

In these embodiments of the method according to the invention, the barrier member is preferably located alongside an internal surface of the cavity, for example using robotic handling. In particular, the barrier member preferably has a shape that matches that internal surface of the mould cavity. The barrier member may be formed with a shape that matches the internal surface of the mould cavity, against which the barrier member will be located. Alternatively, the barrier member may be deformed into a different configuration on, or before, location in the mould cavity, or even during injection moulding in that cavity. For instance, the barrier member may be formed with a substantially planar configuration, and then located within the first mould cavity in an arcuate or tubular configuration, before either the sealing member or the main body of the device is formed by injection moulding in that cavity. In particular, the barrier member may be cut or stamped from a sheet of barrier material, or may be formed by injection moulding. Where necessary, the barrier member held in position by suitable retaining means. Such retaining means may comprise electrostatic attraction, vacuum suction and/or sharp pins in the cavity.

In alternative embodiments of the method according to the invention, the barrier member may be formed by spraying or painting barrier material, whilst uncured or unsolidified, onto the internal surface of the mould cavity. In this embodiment, the sealing member or the main body of the device may then be formed by injection moulding in that cavity, such that that component bonds to the barrier member. As in the embodiments described above, the partially-formed device is preferably then transferred to a second mould cavity, and the remaining component, ie either the sealing member or the main body of the device, is preferably formed by injection moulding in that cavity, such that that component also bonds to the barrier member.

In further alternative embodiments of the method according to the invention, the barrier member may be bonded to either the sealing member or the main body of the device whilst the barrier member, at least, is incompletely cured or solidified. For instance, the barrier member may be bonded to the sealing member and/or the main body of the device by bringing those components into contact with each other whilst they are both incompletely cured or solidified. In particular, the barrier member may be bonded to the sealing member and/or the main body of the device in a multi-shot injection moulding process. In these embodiments, the barrier member is preferably formed of a plastics material or a thermoplastic elastomer.

Another alternative method for bonding the barrier member to the sealing member and/or the main body of the device comprises welding the barrier member to that component. In particular, the welding step may involve the use of suitable heating means, such as a fluid at an increased temperature relative to the barrier member, eg a jet of hot air, or electromagnetic radiation, eg from a laser, to heat at least one of the engagement surfaces that are to be bonded together.

The engagement surfaces of the barrier member and the component to which it is to be welded, ie the sealing member or the main body of the device, may be heated before those surfaces are brought into engagement with each other. In these embodiments, either the sealing member or the main body of the device is preferably welded to a first engagement surface of the barrier member, and the other component is preferably then welded to a second engagement surface of the barrier member.

Alternatively, the engagement surfaces of the barrier member and the component(s) to which it is to be welded may be brought into engagement with each other before any heating, such that the engagement surfaces are adjacent to each other, and the barrier member may then be heated using electromagnetic radiation, eg using a laser, in order to weld the barrier member to the component(s). In particular, the barrier member, the sealing member and the main body of the device may be assembled together, and then bonded together by heating the barrier member until it is welded to the sealing member and the main body of the device. In these embodiments, the barrier member is preferably adapted to absorb a selected electromagnetic radiation, eg from a laser, to a sufficient extent for adjacent engagement surfaces to become welded together. In contrast, the sealing member and/or the main body of the device are preferably adapted to transmit the selected electromagnetic radiation to a sufficient extent that those components are not heated to a significant degree by the selected electromagnetic radiation, and in particular are not adversely affected by that radiation during manufacture.

According to a further aspect of the invention, there is provided a respiratory interface device comprising a main body that includes a fluid conduit adapted to be connected to a breathing circuit, and a sealing member adapted to engage a surface of a patient, such that the fluid conduit is in fluid communication, in use, with an airway of the patient, the sealing member including a first plasticising agent, and the main body of the device including a second plasticising agent, wherein the first and second plasticising agents are adapted so as to impede migration of the first plasticising agent from the sealing member to the main body of the device and/or impede migration of the second plasticising agent from the main body of the device to the sealing member.

The first and second plasticising agents are preferably immiscible. This may be achieved by the first and second plasticising agents having different molecular weights. Alternatively, the compounds of the first and second plasticising agents may differ in polarity or atomicity.

According to a further aspect of the invention, there is provided a breathing circuit comprising a respiratory interface device as described above.

Preferred embodiments of the invention will now be described in greater detail, by way of illustration only, with reference to the accompanying drawings, in which.

Figure 1:
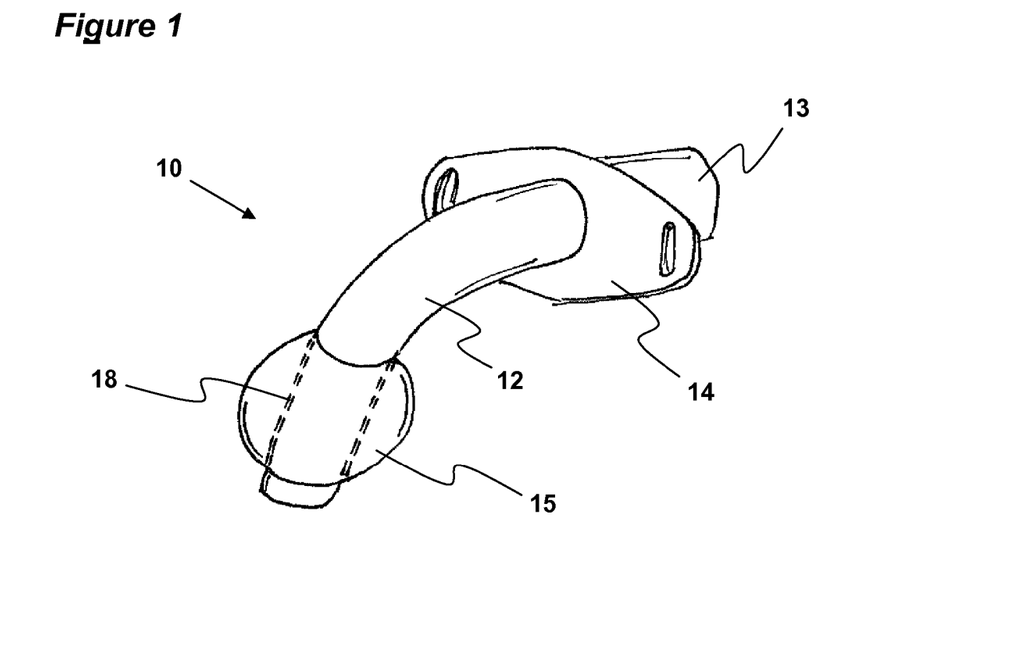
FIG. 1 is a perspective view of a tracheostomy tube according to the present invention, which shows hidden detail.

FIG. 1 shows a tracheostomy tube according to the present invention, which is generally designated 10. The tracheostomy tube 10 comprises a fluid conduit defined by a tubular passageway 12, which is arcuate in form. The tubular passageway 12 includes a connector 13 at one end that is adapted to connect the tracheostomy tube 10 to a breathing circuit. The tracheostomy tube 10 also includes an elongate flange 14, which is disposed adjacent to the connector 13. The flange 14 includes an opening at each end for engagement with a strap (not shown in the Figures), which secures the tracheostomy tube 10 to the patient.

At the other end of the tubular passageway 12, a sealing member 15 surrounds a portion of the tubular passageway 12. The sealing member 15 has a circular cross-section, and an external surface that is generally convex in form along its longitudinal axis. In addition, a tubular barrier member 18 is interposed between the exterior surface of the tubular passageway 12 and the interior surface of the sealing member 15, such that the tubular passageway 12 and the sealing member 15 are not in direct contact.

The tubular passageway 12, the connector 13 and the flange 14 are formed of Styrene Ethylene Butylene Styrene (SEBS) including white paraffin oil as a plasticising agent. Similarly, the sealing member 15 is formed of SEBS including white paraffin oil as a plasticising agent. However, the sealing member 15 is formed with a significantly greater concentration of plasticising agent, relative to the tubular passageway 12, the connector 13 and the flange 14. In order to substantially prevent the migration of plasticising agent from the sealing member 15 to the tubular passageway 12, the barrier member 18 is formed of Ethylene Vinyl Alcohol (EVOH) and polypropylene. In particular, the barrier member 18 has a central tubular layer of Ethylene Vinyl Alcohol (EVOH), which is highly effective at preventing the migration of plasticiser therethrough. In addition, in order to ensure that the barrier member 18 bonds effectively to both the sealing member 15 and the tubular passageway 12, the barrier member 18 includes an outer tubular layer and an inner tubular layer that are both formed of polypropylene. Hence, it is the polypropylene layers of the barrier member 18 that bond to the sealing member 15 and the tubular passageway 12.

During manufacture, the tubular barrier member 18 is firstly formed from a flexible sheet of pre-formed barrier material, having a central layer of Ethylene Vinyl Alcohol (EVOH) and outer layers of polypropylene, which is then introduced into a first cavity of a mould in a tubular arrangement. In particular, the sheet of pre-formed barrier material is wrapped into a tubular configuration, and positioned in the first cavity, where it is retained by electrostatic attraction, vacuum suction or sharp pins in the cavity.

The tubular passageway 12, the connector 13 and the flange 14 are then formed in the first cavity by injection moulding, such that the tubular passageway 12 bonds to the interior surface of the barrier member 18. The partially-formed tracheostomy tube is then transferred into a second cavity of the mould, and the sealing member 15 is formed by injection moulding, such that the sealing member 15 bonds to the exterior surface of the barrier member 12.

Figure 2:
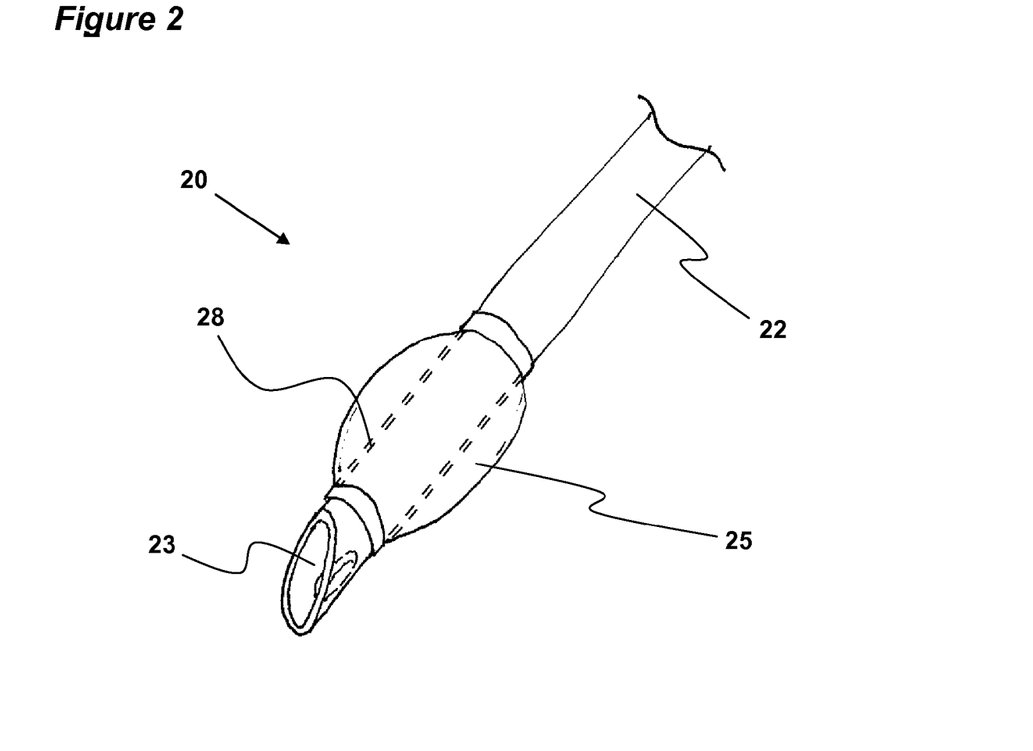
FIG. 2 is a fragmentary, perspective view of an endotracheal tube according to the present invention, which shows hidden detail.

FIG. 2 shows an endotracheal tube according to the present invention, which is generally designated 20. The endotracheal tube 20 comprises a fluid conduit defined by a tubular passageway 22 including a tip 23 at one end, a sealing member 25 and a tubular barrier 28. The sealing member 25 surrounds a portion of the tubular passageway 22 adjacent to the tip 23. The sealing member 25 has a circular cross-section, and an external surface that is generally convex in form along its longitudinal axis. In addition, the tubular passageway 22 includes a connector (not shown in FIG. 1) at the opposite end of the tube 22 to the sealing member 25, which is adapted to connect the endotracheal tube 20 to a breathing circuit.

A tubular barrier member 28 is interposed between the exterior surface of the tubular passageway 22 and the interior surface of the sealing member 25, such that the tubular passageway 22 and the sealing member 25 are not in direct contact.

In a similar arrangement to the tracheostomy tube 10 shown in FIG. 1, the sealing member 25 and the tubular passageway 22 are both formed of Styrene Ethylene Butylene Styrene (SEBS), including white paraffin oil as a plasticising agent, but the sealing member 25 is formed with a significantly greater concentration of plasticising agent relative to the tubular passageway 22. Furthermore, in order to substantially prevent the migration of plasticising agent from the sealing member 25 to the tubular passageway 22, the barrier member 28 has an identical configuration to the barrier member 18 of the tracheostomy tube 10 shown in FIG. 1.

During manufacture, the tubular barrier member 28 is formed within a first cavity of a mould by the same method described above in relation to the tracheostomy tube 10. The tubular passageway 22 is then formed in the first cavity by injection moulding, such that the tubular passageway 22 bonds to the interior surface of the barrier member 28. The partially-formed endotracheal tube is then transferred into a second cavity of the mould, and the sealing member 25 is formed by injection moulding, such that the sealing member 25 bonds to the exterior surface of the barrier member 22.

Figure 3:
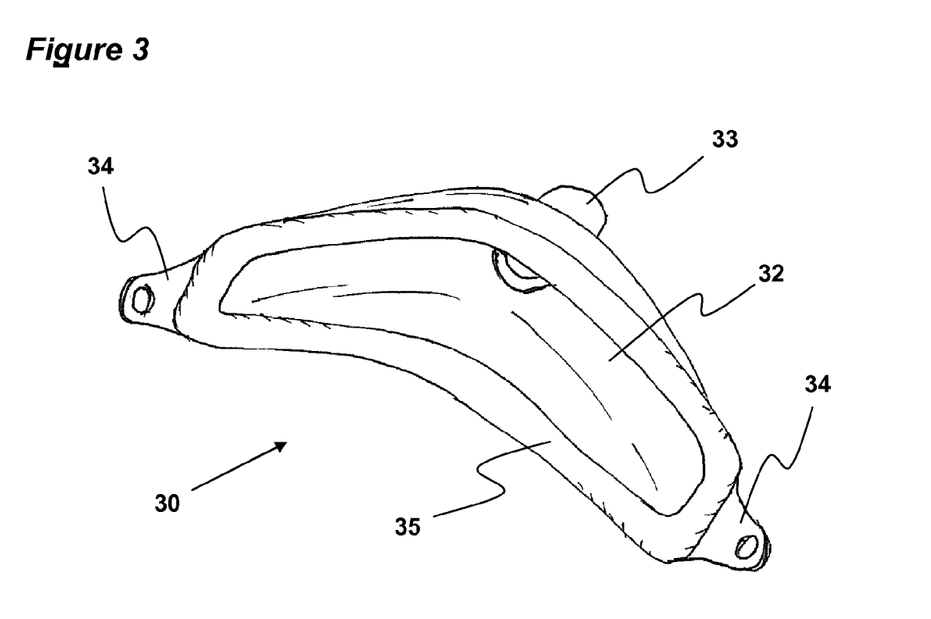
FIG. 3 is a perspective view of a tracheostomy mask according to the present invention.
Figure 4:
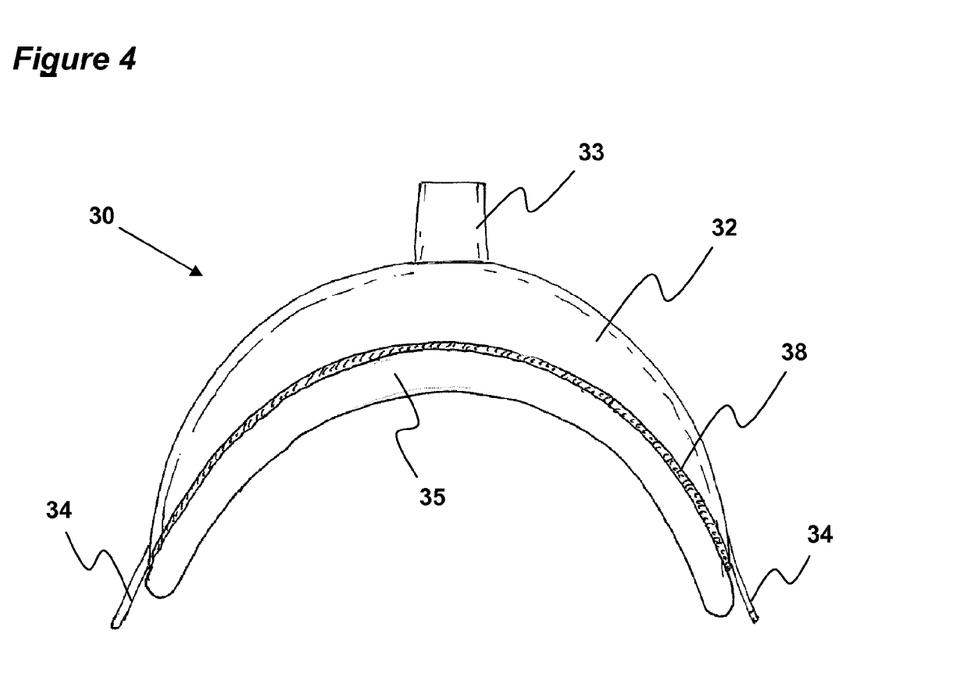
FIG. 4 is a plan view of the tracheostomy mask of FIG. 3.

FIGS. 3 and 4 show a tracheostomy mask according to the present invention, which is generally designated 30. The tracheostomy mask 30 comprises a mask body 32 that defines a cavity from which a patient may withdraw respiratory gases, and a sealing member 35 disposed about a peripheral edge of the mask body 32 for sealing the mask body 32 to the skin of a patient. The mask body 32 also includes a connector 33 for connecting the mask body 32 to a breathing circuit, and a pair of flanges 34 at each end of the mask body 32, each including an opening, for engagement with a retaining strap (not shown in the Figures) for securing the tracheostomy mask 30 to a patient.

The sealing member 35 is a non-inflatable member having a substantially circular cross-section and a closed-loop configuration. In addition, the mask body 32 includes a circumferential flange (not visible in the Figures) that surrounds the opening into the cavity of the mask body 32. A barrier member 38 is interposed between the sealing member 35 and the circumferential flange of the mask body 32, such that the sealing member 35 and the mask body 32 are not in direct contact. In particular, the sealing member 35 is bonded to a continuous engagement surface on one side of the barrier member 38, and the circumferential flange of the mask body 32 is bonded to a separate, continuous engagement surface on the other side of the barrier member 38.

In a similar arrangement to the respiratory interface devices 10,20 described above, the mask body 32, the connector 33, the flanges 34 and the sealing member 35 are each formed of Styrene Ethylene Butylene Styrene (SEBS), including white paraffin oil as a plasticising agent, but with the sealing member 25 being formed with a significantly greater concentration of plasticising agent relative to the mask body 32.

In order to substantially prevent the migration of plasticising agent from the sealing member 35 to the mask body 32, the barrier member 38 has a similar form to the barrier members 18,28 of the tracheostomy tube 10 and the endotracheal tube 20 described above. In particular, the barrier member 38 is formed of Ethylene Vinyl Alcohol (EVOH) and polypropylene. In particular, the barrier member 38 has a central layer of Ethylene Vinyl Alcohol (EVOH), which is highly effective at preventing the migration of plasticiser therethrough. In addition, in order to ensure that the barrier member 38 bonds effectively to both the sealing member 35 and the mask body 32, the barrier member 38 includes outer layers, on both sides of the central layer, that are formed of polypropylene. Hence, it is the polypropylene layers of the barrier member 38 that bond to the sealing member 35 and the mask body 32.

During manufacture, the barrier member 38 is firstly stamped from a flexible sheet of pre-formed barrier material, having a central layer of Ethylene Vinyl Alcohol (EVOH) and outer layers of polypropylene, and then introduced into a first cavity of a mould. In particular, the barrier member 38 is arranged alongside an internal surface of the first cavity, where it is retained by electrostatic attraction, vacuum suction or sharp pins in the cavity.

The mask body 32, the connector 33 and the flanges 34 are then formed in the first cavity by injection moulding, such that the mask body 32 bonds to an outer layer of the barrier member 38. The partially-formed tracheostomy mask is then transferred into a second cavity of the mould, and the sealing member 35 is formed by injection moulding, such that the sealing member 35 bonds to the other outer layer of the barrier member 38.

Figure 5:
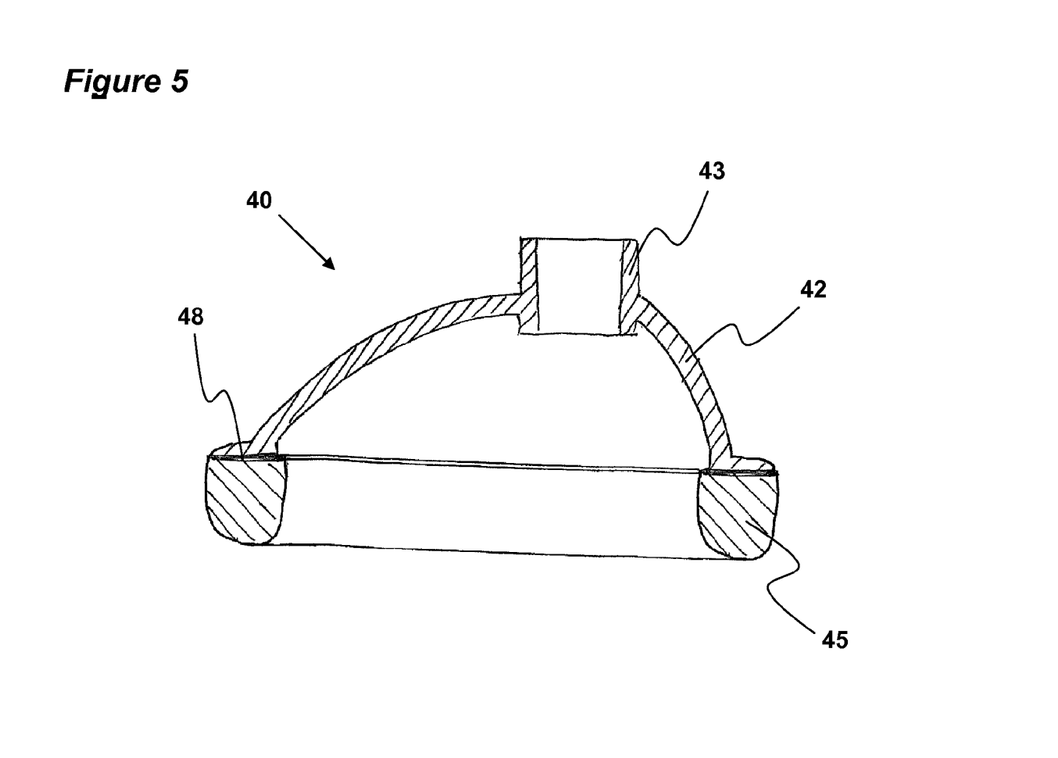
FIG. 5 is a cross-sectional view of a respiratory mask according to the invention.

FIG. 5 shows a respiratory mask according to the present invention, which is generally designated 40. The respiratory mask 40 comprises a mask body 42 that defines a cavity adapted to accommodate a patient's nose and mouth, and a sealing member 45 adapted to seal the mask 40 against a portion of skin surrounding the patient's nose and mouth. The mask body 42 also includes a connector 43 adapted to connect the respiratory mask 40 to a breathing circuit.

The sealing member 45 is a non-inflatable member having a closed-loop configuration. In addition, the mask body 42 includes a circumferential flange that surrounds an opening into the cavity of the mask body 42. A barrier member 48 is interposed between the sealing member 45 and the circumferential flange of the mask body 42, such that the sealing member 45 and the mask body 42 are not in direct contact. In particular, the sealing member 45 is bonded to a continuous engagement surface on one side of the barrier member 48, and the circumferential flange of the mask body 42 is bonded to a separate, continuous engagement surface on the other side of the barrier member 48.

In a similar arrangement to the respiratory interface devices 10,20,30 described above, the sealing member 45 and the mask body 42 are both formed of Styrene Ethylene Butylene Styrene (SEBS), including white paraffin oil as a plasticising agent, but the sealing member 45 is formed with a significantly greater concentration of plasticising agent relative to the mask body 42. Furthermore, in order to substantially prevent the migration of plasticising agent from the sealing member 45 to the mask body 42, the barrier member 48 has the same multi-layered configuration as the barrier member 38 of the tracheostomy mask 30 discussed above.

During manufacture, the barrier member 48 is firstly stamped from a sheet of pre-formed barrier material, having a central layer of Ethylene Vinyl Alcohol (EVOH) and outer layers of polypropylene, and then introduced into a first cavity of a mould. In particular, the barrier member 48 is arranged alongside an internal surface of the first cavity, where it is retained by electrostatic attraction, vacuum suction or sharp pins in the cavity.

The mask body 42 is then formed in the first cavity by injection moulding, such that the mask body 42 bonds to an outer layer of the barrier member 48. The partially-formed respiratory mask is then transferred into a second cavity of the mould, and the sealing member 45 is formed by injection moulding, such that the sealing member 45 bonds to the other outer layer of the barrier member 48.

Figure 6:
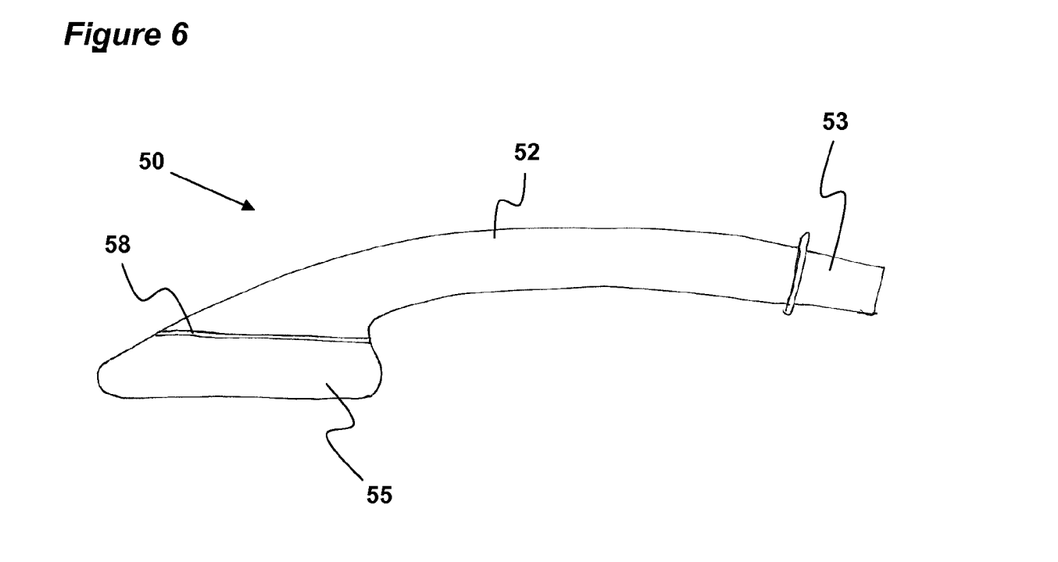
FIG. 6 is a side view of a first embodiment of a supraglottic airway according to the present invention.

FIG. 6 shows a first embodiment of a supraglottic airway according to the present invention, which is generally designated 50. The supraglottic airway 50 comprises a fluid conduit defined by a tubular passageway 52 and a sealing member 55 disposed at one end of the tubular passageway 52. At the other end of the tubular passageway 52, a connector 53 is provided for connecting the supraglottic airway 50 to a breathing circuit.

The sealing member 55 is non-inflatable, and is formed so that it is a snug fit over the laryngeal inlet of a patient, in use. In addition, the sealing member 55 includes an opening that is co-extensive with the internal bore of the tubular passageway 52. The tubular passageway 52 and its internal bore have substantially constant cross-sections along their length, but these cross-sections increase adjacent to the sealing member 55, such that the opening in the sealing member 55 is enlarged relative to the internal bore of the majority of the tubular passageway 52.

In this embodiment, the end of the tubular passageway 52 that is adjacent to the sealing member 55 is formed with a substantially flat, annular surface, to which an annular barrier member 58 is bonded. Furthermore, the sealing member 55 includes a substantially flat, annular surface that is bonded to the other side of the barrier member 58. In this way, the sealing member 55 and the tubular passageway 52 are not in direct contact.

In a similar arrangement to the respiratory interface devices 10,20,30,40 described above, the tubular passageway 52 and the sealing member 55 are each formed of Styrene Ethylene Butylene Styrene (SEBS), including white paraffin oil as a plasticising agent, but with the sealing member 55 being formed with a significantly greater concentration of plasticising agent relative to the tubular passageway 52.

In order to substantially prevent the migration of plasticising agent from the sealing member 55 to the tubular passageway 52, the barrier member 58 has a similar form to the barrier members 18,28,38,48 of the respiratory interface devices 10,20,30,40 described above. In particular, the barrier member 58 is formed of Ethylene Vinyl Alcohol (EVOH) and polypropylene. In particular, the barrier member 58 has a central layer of Ethylene Vinyl Alcohol (EVOH), which is highly effective at preventing the migration of plasticiser therethrough. In addition, in order to ensure that the barrier member 58 bonds effectively to both the sealing member 55 and the tubular passageway 52, the barrier member 58 includes outer layers, on both sides of the central layer, that are formed of polypropylene. Hence, it is the polypropylene layers of the barrier member 58 that bond to the sealing member 55 and the tubular passageway 52.

During manufacture, the barrier member 58 is firstly stamped from a sheet of pre-formed barrier material, having a central layer of Ethylene Vinyl Alcohol (EVOH) and outer layers of polypropylene, and then introduced into a first cavity of a mould. In particular, the barrier member 58 is arranged alongside an internal surface of the first cavity, where it is retained by electrostatic attraction, vacuum suction or sharp pins in the cavity.

The tubular passageway 52 is then formed in the first cavity by injection moulding, such that the tubular passageway 52 bonds to an outer layer of the barrier member 58. The partially-formed supraglottic airway is then transferred into a second cavity of the mould, and the sealing member 55 is formed by injection moulding, such that the sealing member 55 bonds to the other outer layer of the barrier member 58.

Figure 7:
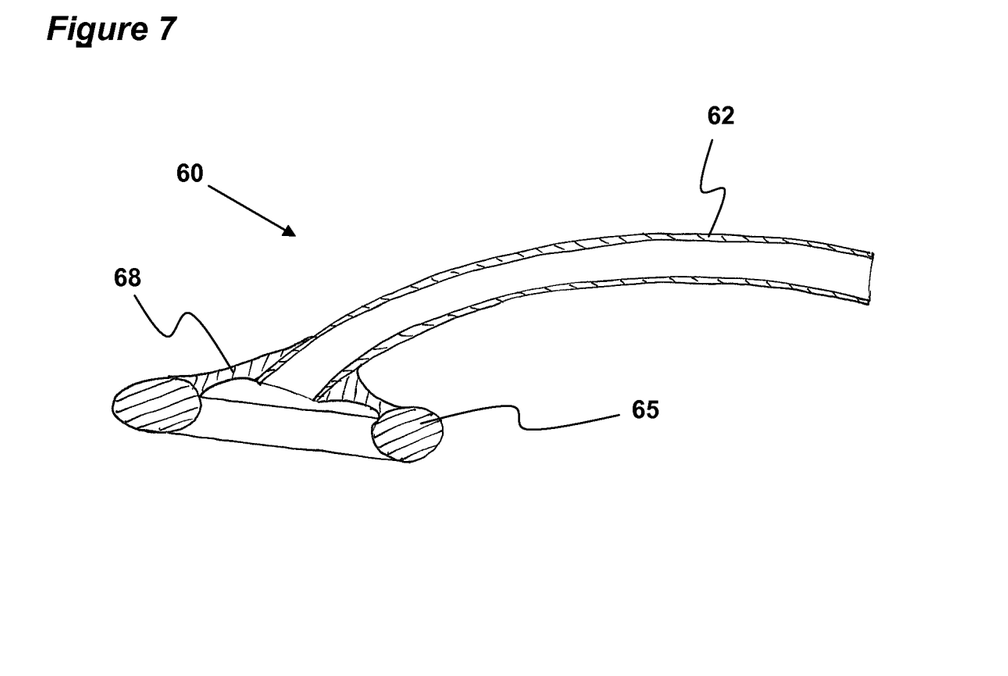
FIG. 7 is a cross-sectional view of a second embodiment of a supraglottic airway according to the present invention.

FIG. 7 shows a second embodiment of a supraglottic airway according to the present invention, which is generally designated 60. This embodiment of a supraglottic airway according to the present invention is identical to the first embodiment shown in FIG. 6, save for the different form of the barrier member 68 and its attachment to the tubular passageway 62 and the sealing member 65.

In particular, the tubular passageway 62 of this embodiment has a constant cross-section along its entire length, and the barrier member 68 is bonded to the external surface of the tubular passageway 62, about its entire circumference at one end of the tubular passageway 62. In addition, the sealing member 65 is annular in form and has a substantially constant, circular cross-section. The barrier member 68 extends outwardly from the exterior surface of the tubular passageway 62, and is bonded to the sealing member 65 along a peripheral engagement surface, which is concave in form so as to receive the sealing member 65 therein.

The materials of this embodiment of a supraglottic airway according to the present invention are identical to the first embodiment of a supraglottic airway according to the invention, which is shown in FIG. 6, save for the barrier member 68 being formed of a single material only. In particular, the barrier member 68 is formed of polypropylene.

This embodiment of a supraglottic airway according to the invention is manufactured by multi-shot injection moulding. In particular, the tubular passageway 62 is firstly formed by injection moulding in a first cavity of the mould. The tubular passageway 62 is then transferred to a second cavity of the mould, and the barrier member 68 is formed by injection moulding, such that the barrier member 68 bonds to the external surface of the tubular passageway 62, as discussed above. The part-formed supraglottic airway is then transferred into a third cavity of the mould, and the sealing member 65 is formed by injection moulding, such that the sealing member 65 bonds to the engagement surface of the barrier member 68.

Figure 8:
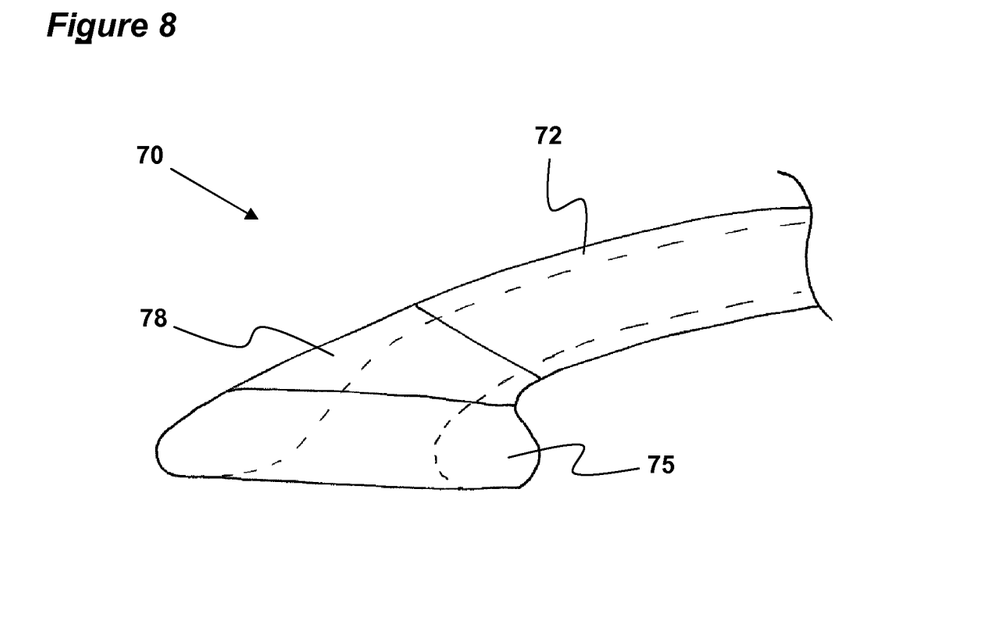
FIG. 8 is a fragmentary, side view of a third embodiment of a supraglottic airway according to the present invention, which shows hidden detail.

FIG. 8 shows a third embodiment of a supraglottic airway according to the present invention, which is generally designated 70. This embodiment of a supraglottic airway 70 according to the present invention has the same general form as the first embodiment shown in FIG. 7. However, in this embodiment, the barrier member 78 defines an intermediate portion of the fluid conduit, with the tubular passageway 72 bonded to a substantially flat, annular engagement surface of the barrier member 78, and the sealing member 75 bonded to a substantially flat, annular engagement surface on the other side of the barrier member 78. These engagement surfaces are inclined relative to each other. In addition, the tubular passageway 72, the sealing member 75 and the barrier member 78 are formed so that the internal bores of these components are co-extensive, and hence the interior bore of the supraglottic airway 70 that defines the fluid conduit is substantially smooth.

The materials of this embodiment of a supraglottic airway according to the present invention are identical to the first embodiment shown in FIG. 6, save for the barrier member 78 being formed of a single material only. In particular, the barrier member 78 is formed of polypropylene.

This embodiment of a supraglottic airway according to the invention is manufactured by multi-shot injection moulding, as described above for the second embodiment. In particular, the tubular passageway 72 is firstly formed by injection moulding in a first cavity of the mould. The tubular passageway 72 is then transferred to a second cavity of the mould, and the barrier member 78 is formed by injection moulding, such that the barrier member 78 bonds to the external surface of the tubular passageway 72, as discussed above. The part-formed supraglottic airway is then transferred into a third cavity of the mould, and the sealing member 75 is formed by injection moulding, such that the sealing member 75 bonds to the engagement surface of the barrier member 78.

Figure 9:
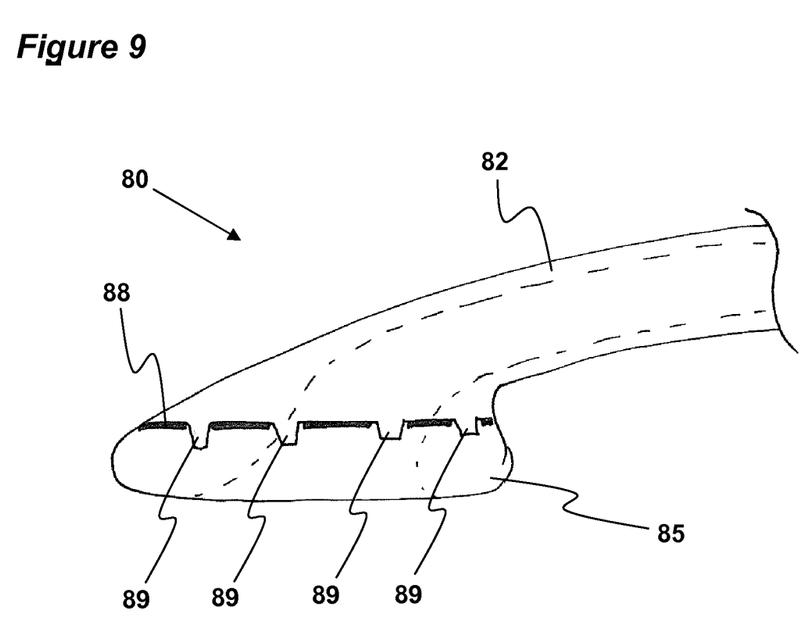
FIG. 9 is a fragmentary, side view of a fourth embodiment of a supraglottic airway according to the present invention, which shows hidden detail.

FIG. 9 shows a fourth embodiment of a supraglottic airway according to the present invention, which is generally designated 80. This embodiment of a supraglottic airway 80 according to the present invention has the same general form as the first embodiment shown in FIG. 6. However, in the fourth embodiment, the barrier member 88 comprises a plurality of openings (four openings are shown in FIG. 9), and the tubular passageway 82 includes a plurality of projections 89 that extend through the openings of the barrier member 88 and are bonded to the material of the sealing member 85. These projections 89 provide effective bonding between the tubular passageway 82 and the sealing member 85, whilst the barrier member 87 significantly impedes the migration of plasticising agent from the sealing member 85 to the tubular passageway 82.

The materials of this embodiment of a supraglottic airway according to the present invention are identical to the first embodiment shown in FIG. 6. In particular, the barrier member 88 is formed of Ethylene Vinyl Alcohol (EVOH) and polypropylene.

During manufacture, the barrier member 88 is firstly stamped from a sheet of pre-formed barrier material, having a central layer of Ethylene Vinyl Alcohol (EVOH) and outer layers of polypropylene, and then introduced into a first cavity of a mould. In particular, the barrier member 88 is arranged alongside an internal surface of the first cavity, where it is retained by electrostatic attraction, vacuum suction or sharp pins in the cavity. The tubular passageway 82 is then formed in the first cavity by injection moulding, such that the tubular passageway 82 bonds to an outer layer of the barrier member 88. The partially-formed supraglottic airway is then transferred into a second cavity of the mould, and the sealing member 85 is formed by injection moulding, such that the sealing member 85 bonds to the other outer layer of the barrier member 88.

The invention claimed is:

1. A respiratory interface device comprising a main body that includes a fluid conduit adapted to be connected to a breathing circuit, and a non-inflatable sealing member adapted to engage a surface of a patient, such that the fluid conduit is in fluid communication, in use, with an airway of the patient, the non-inflatable sealing member and the main body forming an interface where the non-inflatable sealing member and the main body directly contact one another, the non-inflatable sealing member including a first plasticising agent, and the main body of the device including a second plasticising agent, wherein the first and second plasticising agents are adapted so as to: (i) impede migration of the first plasticising agent in a first direction from the non-inflatable sealing member to the main body of the device across the entire interface, (ii) impede migration of the second plasticising agent in a second direction from the main body of the device to the non-inflatable sealing member across the entire interface, or (iii) impede migration of the first plasticising agent in the first direction and migration of the second plasticising agent in the second direction across the entire interface.

2. A respiratory interface device as claimed in any claim 1, wherein the second plasticising agent is present in the main body at a concentration that is lower than a concentration of the first plasticising agent in the non-inflatable sealing member, such that the non-inflatable sealing member is more deformable than the main body of the sealing device.

3. A breathing circuit comprising a respiratory interface device as claimed in claim 1.

4. A respiratory interface device as claimed in claim 1, wherein the respiratory interface device is a supraglottic airway device.

5. A respiratory interface device as claimed in claim 4, wherein the non-inflatable sealing member defines an opening that is in fluid communication with the fluid conduit, and the opening is enlarged relative to an internal bore of the majority of the fluid conduit.

6. A respiratory interface device as claimed in claim 1, wherein the first and second plasticising agents are immiscible.

7. A respiratory interface device as claimed in claim 6, wherein the first and second plasticising agents have different molecular weights.

8. A respiratory interface device as claimed in claim 6, wherein the compounds of the first and second plasticising agents differ in polarity or atomicity.

* * * * *